United States Patent
Yamamoto et al.

[11] Patent Number: 6,117,289
[45] Date of Patent: *Sep. 12, 2000

[54] CHOLESTEROL SENSOR AND METHOD FOR PRODUCING THE SAME

[75] Inventors: Tomohiro Yamamoto; Toshihiko Yoshioka; Shiro Nankai, all of Hirakata, Japan

[73] Assignee: Matsushita Electric Industrial Co., Ltd., Osaka, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/986,743

[22] Filed: Dec. 8, 1997

[30] Foreign Application Priority Data

Dec. 20, 1996 [JP] Japan .................. 8-341212

[51] Int. Cl.⁷ .................................. G01N 27/26
[52] U.S. Cl. .......................... 204/403; 427/2.13
[58] Field of Search ............ 204/403; 435/817; 427/2.1, 2.11, 2.12, 2.13

[56] References Cited

U.S. PATENT DOCUMENTS

| | | |
|---|---|---|
| 4,378,429 | 3/1983 | Modrovich . |
| 4,409,326 | 10/1983 | Modrovich ............................ 435/11 |
| 5,141,868 | 8/1992 | Shanks et al. ...................... 435/288 |
| 5,281,323 | 1/1994 | Sugama et al. ..................... 204/415 |
| 5,286,362 | 2/1994 | Hoenes et al. ..................... 204/403 |
| 5,312,590 | 5/1994 | Gunasingham . |
| 5,382,346 | 1/1995 | Uenoyama et al. ................ 204/403 |
| 5,403,745 | 4/1995 | Ollington et al. . |
| 5,426,030 | 6/1995 | Ritterdorf et al. . |
| 5,589,347 | 12/1996 | Arai et al. . |
| 5,695,947 | 12/1997 | Guo et al. .............................. 435/11 |

FOREIGN PATENT DOCUMENTS

| | | |
|---|---|---|
| 0230786 | 12/1986 | European Pat. Off. . |
| 0310824 | 9/1988 | European Pat. Off. . |
| 0794429 | 3/1997 | European Pat. Off. . |
| 62-088952 | 4/1987 | Japan . |
| 63-080842 | 4/1988 | Japan . |
| 63-109799 | 5/1988 | Japan . |
| 02062952 | 3/1990 | Japan . |
| 04295755 | 10/1992 | Japan . |
| 06229973 | 8/1994 | Japan . |

OTHER PUBLICATIONS

Chemical abstracts vol. 106, No. 21, May 25, 1987, Cheillan F. et al. "Comparative study on determinaiton fro cholesterol in biological fluids" XP–002059700.

Crumbliss et al. ("A carrageenan hydrogel stabilized colloidal gold multi–enzyme biosensor electrode utilizing immobilized horeseradish peroxidase and cholesterol esterase to detect cholesterol in serum and whole blood", Biosensors & Bioelectronics 8 (1993) 331–337).

*Primary Examiner*—Jill Warden
*Assistant Examiner*—Alex Noguerola
*Attorney, Agent, or Firm*—McDermott, Will & Emery

[57] ABSTRACT

A cholesterol sensor facilitating rapid measurement of serum cholesterol levels is disclosed. The sensor comprises an electrode system composed of at least a measuring electrode and a counter electrode and disposed on an electrically insulating base plate and a reaction layer formed on or in the vicinity of the electrode system. The reaction layer contains cholesterol esterase for catalyzing the conversion of cholesterol ester into cholesterol, cholesterol oxidase and a surfactant.

25 Claims, 7 Drawing Sheets

CHOLESTEROL SENSOR AND METHOD FOR PRODUCING THE SAME

BACKGROUND OF THE INVENTION

The present invention relates to a cholesterol sensor that facilitates rapid and simplified quantitation of cholesterol and cholesterol ester concentrations contained in a sample with accuracy, and a method for producing the same.

Proposed conventional system for simplified quantitation of specific components contained in a sample without requiring dilution or agitation of sample solution includes a biosensor disclosed in Japanese Laid-Open Patent Publication Hei 2-062952.

The biosensor is produced by the steps of forming an electrode system comprising a measuring electrode, a counter electrode and a reference electrode by screen printing or the like on an electrically insulating base plate, and disposing thereon an enzyme reaction layer containing a hydrophilic polymer, an oxidoreductase, and an electron mediator. The enzyme reaction layer may further contain a buffer, if necessary.

Upon dropping aliquots of a sample solution containing a substrate over the enzyme reaction layer of such biosensor, the enzyme reaction layer dissolves, causing reaction between the enzyme and the substrate, and reduction of the electrode mediator will result. Upon completion of enzyme reaction, the reduced electron mediator is electrochemically oxidized. The concentration of the substrate in the sample solution can be determined by measuring the oxidation current value at that time.

Theoretically, this biosensor can be applied in measuring various substances if an appropriate enzyme of which substrate is the target of measurement is selected. For example, the use of cholesterol oxidase as the oxidoreductase facilitates production of a biosensor for measuring serum cholesterol levels.

However, the serum cholesterol level used as a diagnostic index represents a sum of cholesterol and cholesterol ester concentrations. Cholesterol ester per se can not serve as the substrate for causing oxidation reaction by cholesterol oxidase. Therefore, for the measurement of the serum cholesterol level as a diagnostic index, cholesterol ester should be converted to cholesterol by some means. Cholesterol esterase is a known catalyzing enzyme for this conversion.

However, the use of cholesterol esterase as the catalyst for converting cholesterol ester to cholesterol necessitates a problem of very slow reaction.

BRIEF SUMMARY OF THE INVENTION

In view of the problem as discussed above, the present invention is aimed at providing a cholesterol sensor that facilitates rapid measurement of cholesterol level by improving cholesterol esterase activities.

The present invention provides a cholesterol sensor comprising an electrically insulating base plate, an electrode system having at least a measuring electrode and a counter electrode formed on the base plate, and a reaction layer formed on or in the vicinity of the electrode system, the reaction layer containing cholesterol oxidase, cholesterol esterase and a surfactant.

In a preferred mode of the present invention, the cholesterol sensor further comprises a cover member for forming a sample solution supply pathway for supplying a sample solution to the electrode system between the cover member and the base plate by being integrated with the base plate.

Basically, the reaction layer preferably has one of the three structures as listed below:
1. The reaction layer has a layer containing a mixture of various components.
2. The reaction layer has two layers; a layer containing cholesterol oxidase and a layer containing cholesterol esterase and a surfactant.
3. The reaction layer has two layers; a layer containing cholesterol oxidase and cholesterol esterase and a layer containing a surfactant for covering the former.

Preferably, in the last-mentioned structure, the layer containing cholesterol oxidase and cholesterol esterase contains no surfactant.

In a preferred cholesterol sensor of the present invention, the electrode system comprises silver and carbon for covering the silver. In this configuration, the surface of the electrode system is preferably coated with a hydrophilic polymer.

The method for producing a cholesterol sensor in accordance with the present invention comprises the steps of:
forming a hydrophilic polymer layer over an electrode system composed of silver and carbon that covers the silver and formed on an electrically insulating base plate,
forming an enzyme layer by adding aliquots of a solution containing only cholesterol oxidase and cholesterol esterase but no surfactant over the previously formed hydrophilic polymer layer, followed by drying, and
forming a layer containing a surfactant by adding aliquots of a solution prepared by dissolving a surfactant in a solvent that would not dissolve the layer of cholesterol oxidase and cholesterol esterase, over the enzyme layer.

While the novel features of the invention are set forth particularly in the appended claims, the invention, both as to organization and content, will be better understood and appreciated, along with other objects and features thereof, from the following detailed description taken in conjunction with the drawings.

DETAILED DESCRIPTION OF THE INVENTION

As discussed above, the cholesterol sensor in accordance with the present invention comprises a reaction layer containing cholesterol oxidase, cholesterol esterase, and further a surfactant.

Upon supply of a sample solution to the reaction layer, the cholesterol ester contained in the sample solution is converted to cholesterol by the catalytic action of the cholesterol esterase activated by the surfactant in the reaction layer.

The cholesterol produced from the cholesterol ester and the cholesterol originally contained in the sample solution are oxidized by the enzyme, cholesterol oxidase. The resultant oxidation reaction causes movement of electrons which in turn act to reduce the electron mediator. The current values required for oxidizing such reduced electron mediator to the original oxidant represents the concentrations of cholesterol ester and cholesterol in the sample solution.

When a voltage is applied to the measuring electrode in order to oxidize the electron mediator, oxidation-reduction reaction may sometimes occur by the electrodes of the cholesterol sensor, producing an error in the oxidation current value measured.

In view of the above, although it is preferable to form the electrode system from an electrochemically stable metal such as platinum, it costs high. Therefore, in producing disposable sensors, it is conventional to assemble an electrode system by forming a silver electrode using a silver paste and subsequently coating it with a carbon paste. However, the carbon layer of a carbon paste is composed of carbon particles and a binder. This structure sometimes permits permeation of a solution containing a surfactant between carbon particles. As a result, when the reaction layer containing the surfactant is dissolved upon addition of a sample solution to the reaction layer, the dissolved solution may enter between the carbon particles and can contact the silver electrode. At that time, if a voltage is applied to the measuring electrode, the silver electrode will be oxidized and generates current, producing a positive error in the current value measured.

In order to suppress such adverse events, there are such methods to cover the electrode system with the hydrophilic polymer layer, or, alternatively, to form the surfactant containing layer, spaced apart from the electrode system.

The former is considerably effective if the concentration of the hydrophilic polymer is well considered. However, since complete blocking of the permeation of the surfactant is impossible with this method, the latter is considered more desirable. Particularly, in consideration of highly efficient enzyme reaction and electrode reaction, it is better to form the surfactant containing layer so as to cover the enzyme layer of cholesterol oxidase and cholesterol esterase, and omit the surfactant from the enzyme layer.

In configuring these reaction layers, it is preferable to form the surfactant layer by dissolving a surfactant in a solvent that would not dissolve the enzyme layer, and subsequently drop the resultant solution over the enzyme layer and dry it.

In the present invention, Nocardia-derived enzymes were used as the cholesterol oxidase and Pseudomonas- or mammalian pancreas-derived enzymes as the cholesterol esterase.

The hydrophilic polymer may be exemplified as carboxymethyl cellulose, polyvinyl pyrrolidone, polyvinyl alcohol, water-soluble cellulose derivatives and the like. Particularly, ethyl cellulose, hydroxypropyl cellulose, gelatin, polyacrylic acid and salts thereof, starch and derivatives thereof, maleic anhydride and salts thereof, polyacrylamide, methacrylic resin, poly-2-hydroxyethylmethacrylate and the like can be used in the present invention.

As the electron mediator, potassium ferricyanide, p-benzoquinone, phenazine methosulfate, ferrocene and the like may be used. The electron mediator is not necessarily an essential requisite, because the oxygen dissolved in a sample solution can be used as the electron mediator if the electrode-related segment is formed from platinum by a sputtering method or the like. In this case, the oxygen contained in the substrate solution is reduced by enzyme reaction to produce hydrogen peroxide, so that the cholesterol concentration in the sample solution can be quantified by detecting the hydrogen peroxide produced with -the platinum electrode.

Preferred surfactant may be exemplified as n-octyl-β-D-thioglucoside, polyethylene glycol monododecylether, sodium cholate, dodecyl-β-maltoside, sucrose monolaurate, sodium deoxycholate, sodium taurodeoxycholate, polyoxyehtylene-p-t-octylphenylether, N,N-bis(3-D-gluconamidopropyl)cholamide, N,N-bis(3-D-gluconamidopropyl)deoxycholamide, and the like.

In order to improve the catalytic activity of cholesterol esterase by adding a surfactant, a combination of Pseudomonas-derived cholesterol esterase with at least one surfactant selected from the group consisting of n-octyl-octyl-β-D-thioglucoside, polyethylene glycol monododecylether, sodium cholate, dodecyl-β-maltoside, sucrose monolaurate, polyoxyehtylene-p-t-octylphenylether and N,N-bis(3-D-gluconamidopropyl)cholamide is preferable.

A similar effect can result from a combination of cholesterol esterase derived from the pancreas of mammals such as calf or swine with at least one surfactant selected from the group consisting of sodium cholate, sodium deoxycholate, sodium taurodeoxycholate, N,N-bis(3-D-gluconamidopropyl)cholamide, N,N-bis(3-D-gluconamidopropyl)deoxycholamide, polyoxyehtylene-p-t-octylphenylether, polyethylene glycol monododecylether and sucrose monolaurate.

The reaction layer of the cholesterol sensor in accordance with the present invention preferably includes a lipid containing layer formed thereon for facilitating introduction of a sample solution into the reaction layer. The lipid containing layer is however not essential for causing the enzyme reaction in the present invention. The lipid is preferably phospholipids including lecithin, phosphatidyl serine, phosphatidyl ethanolamine and the like. More preferable lipids are those with amphiphilic property.

The oxidation current can be measured by either a two-electrode system comprising only a measuring electrode and a counter electrode or a three-electrode system further comprising a reference electrode, in addition to the two electrodes. The latter can measure more accurately.

The arrangement of the reaction layer can be modified in various ways. In other words, the reaction layer can be formed on the electrode system or on a surface exposed to the sample solution supply pathway formed by the cover member. Alternatively, it can be split into two parts, one on the electrode system and the other on the cover member.

In the following, preferred configurations of the cholesterol sensor in accordance with the present invention will be described more specifically, referring to the drawings.

Figure 1:
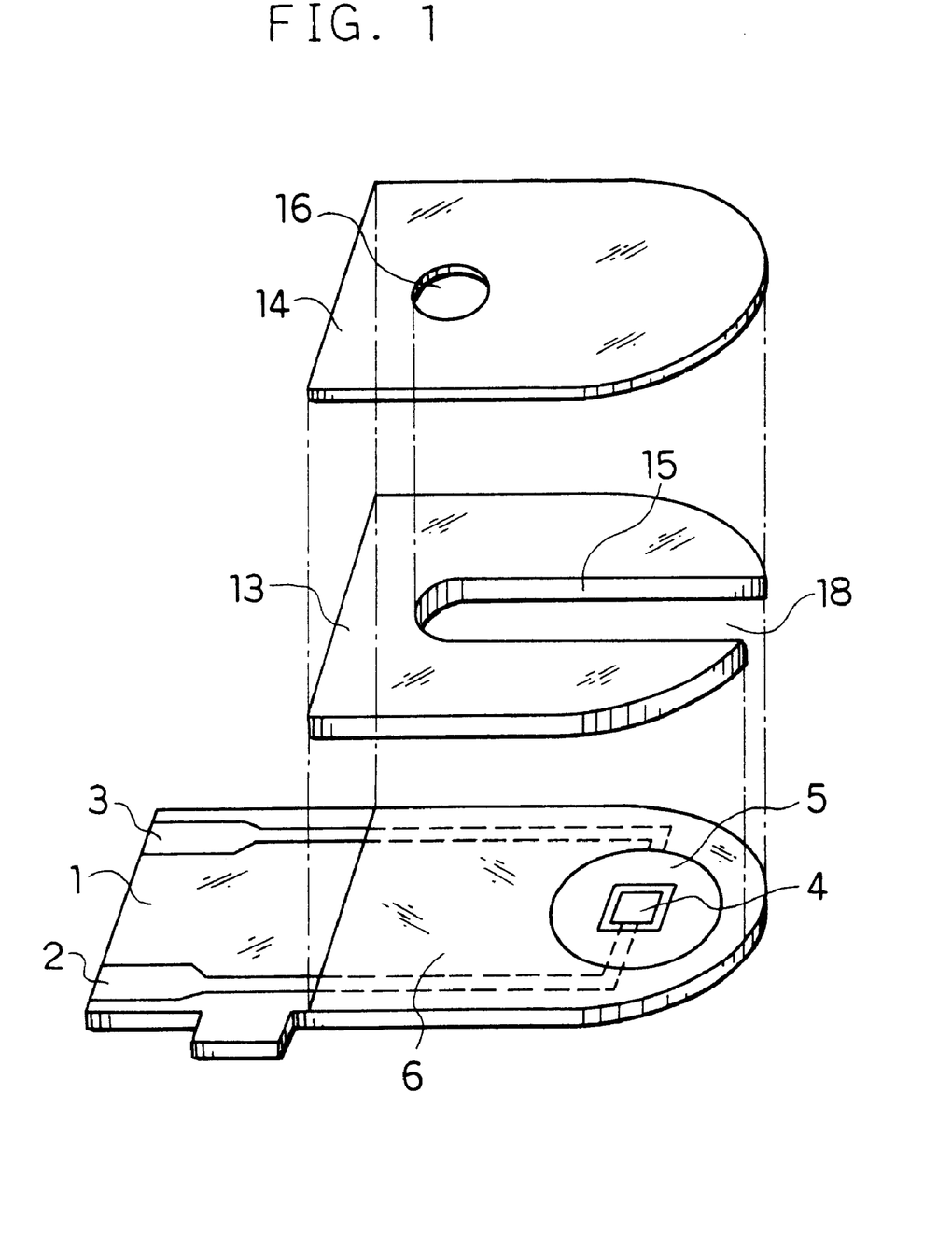
FIG. 1 is a broken oblique perspective view illustrating a cholesterol sensor from which a reaction layer has been omitted of one example in accordance with the present invention.

FIG. 1 is a broken oblique perspective view of a cholesterol sensor in accordance with the present invention from which the reaction layer has been omitted. Numeral 1 designates an electrically insulating base plate made of polyethylene terephthalate. On the base plate 1, leads 2 and 3 are formed by screen-printing a silver paste. The base plate 1 is then further disposed with an electrode system comprising a measuring electrode 4 and a counter electrode 5 by printing a conductive carbon paste containing a resin binder, and an electrically insulating layer 6 by printing an electrically insulating paste. The measuring electrode 4 is connected to the lead 2 and the counter electrode 5 to the lead 3, respectively. The electrically insulating layer 6 functions to hold constant areas of the exposed segments of the measuring electrode 4 and the counter electrode 5, while covering some parts of the leads. Then, the electrically insulating layer 1 formed thereon with the electrode system on which a reaction layer is provided in a manner as described later, a cover 14 having an air vent 16, and a spacer 13 are adhered to each other in a positional relationship as shown by the dotted line in FIG. 1. In this way, a cholesterol sensor can be produced.

In the cholesterol sensor thus produced, a space or cavity for constituting a sample solution supply pathway in a slit 15 of the spacer 13 can be formed between the base plate 1 and the cover 14. Only by simply exposing a sample solution to a tip end 18 of the slit 15 serving as an opening, the sample solution can be readily passed toward the reaction layer through the sample solution supply pathway. Since the sample supply amount depends on the volume of the space formed between the cover and the spacer, pre-quantitation of the sample solution is unnecessary. In addition, since this configuration facilitates minimal evaporation of the sample solution during measurements, the measurement can be done with high accuracy. If a transparent polymer material is used for the cover and the spacer, the condition of the reaction layer and the process how the sample solution is passed through can be observed easily from the outside.

Figure 2:
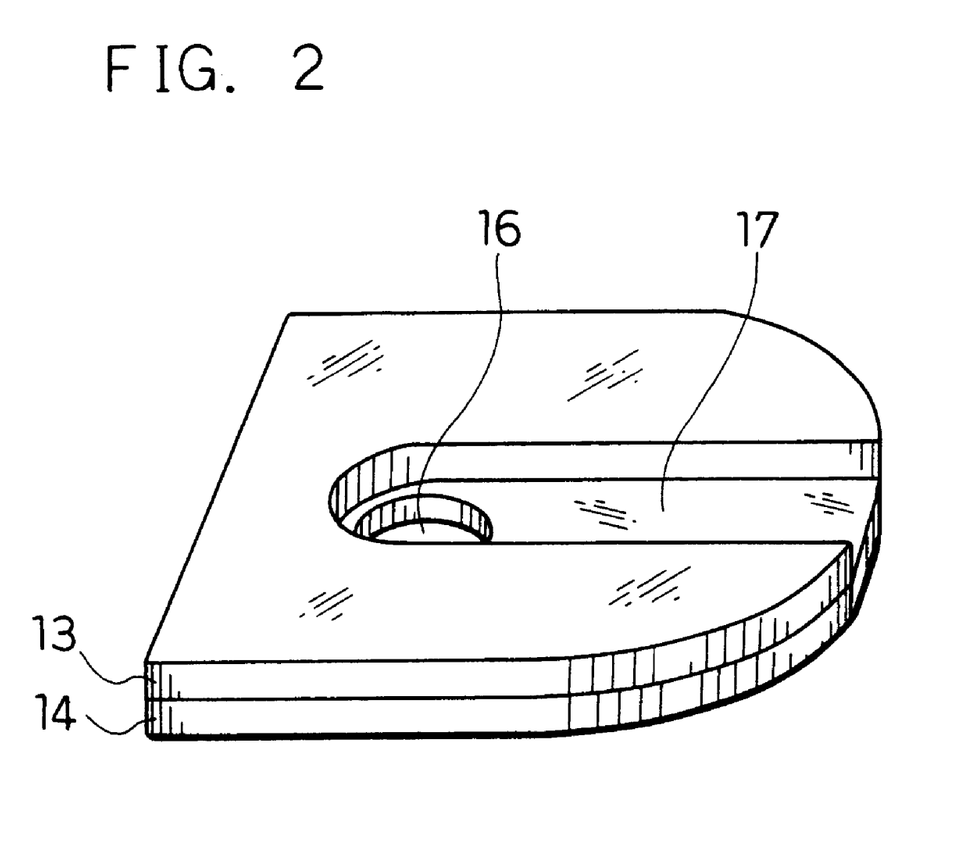
FIG. 2 is an oblique perspective view showing a cover member serving as a cover as well as a spacer of the same cholesterol sensor, with an upside down arrangement of FIG. 1.

FIG. 2 shows an oblique perspective view of a cover member of the same cholesterol sensor in which the spacer 14 and the cover 14 are overlapped, with an upside down arrangement of FIG. 1. A space for constituting the sample solution supply pathway is formed by integrating the cover member with the base plate. Numeral 17 designates a surface on the cover side exposed to this space.

Figure 3:
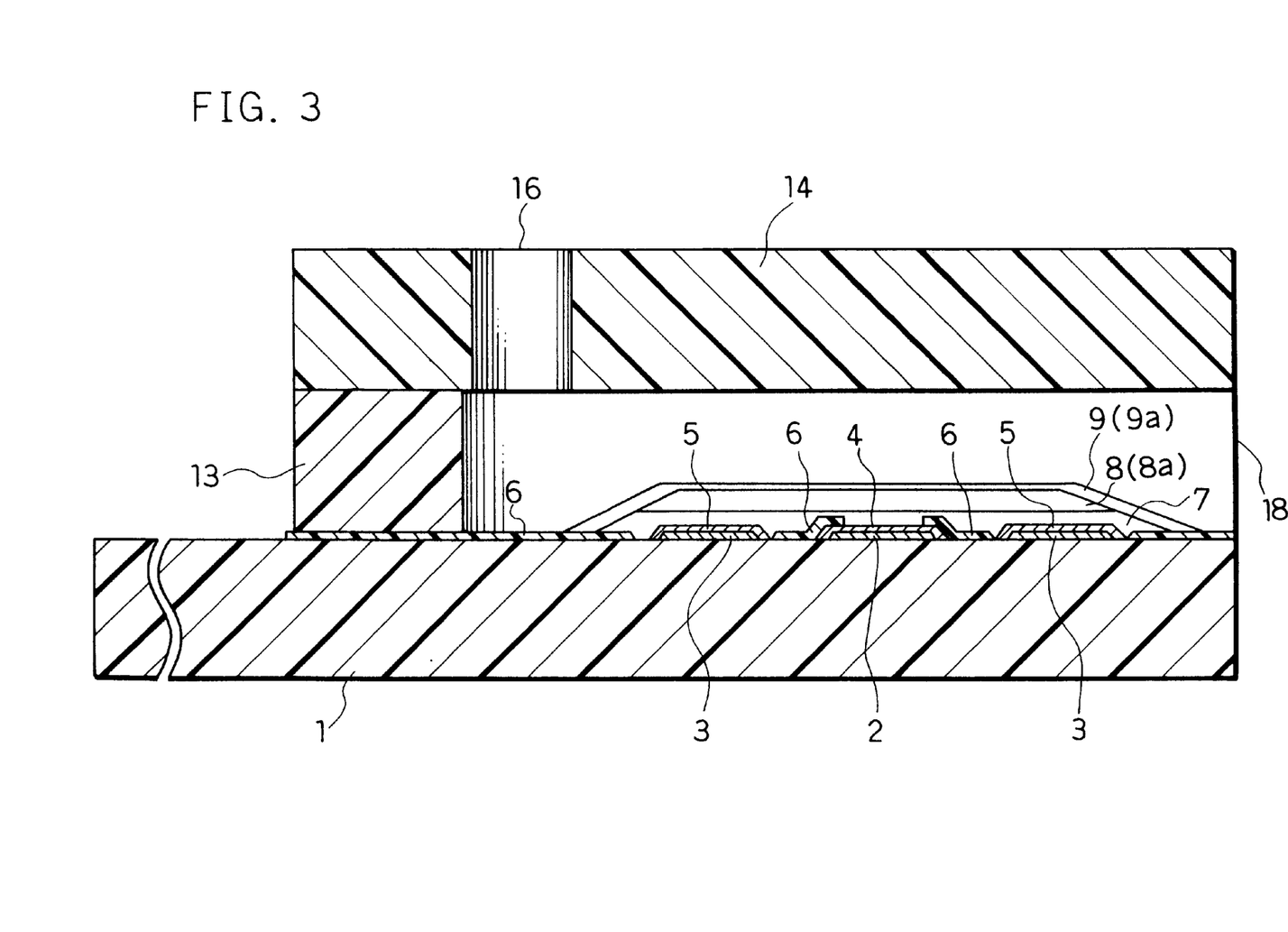
FIG. 3 is a longitudinal cross-sectional view illustrating the vital parts of the same cholesterol sensor.

FIG. 3 illustrates a structure of cholesterol sensors of a first and a second examples in accordance with the present invention.

The cholesterol sensor of the first example comprises the hydrophilic polymer layer 7 formed on the electrode system and the layer 8 containing enzymes formed by dropping aliquots of a solution prepared by dissolving those enzymes on the previously formed hydrophilic polymer layer 7, followed by drying. The enzyme layer 8 contains enzymes, cholesterol oxidase and cholesterol esterase, and further a surfactant. This layer can further contain an electron mediator, if occasion demands.

For smooth introduction of the sample solution into the reaction layer, a layer 9 containing a lipid is formed by dropping a lipid containing solution on the enzyme layer 8 and drying it.

In the absence of agitation in the process of forming the enzyme layer 8, the layer 7 containing the hydrophilic polymer is absolutely unlikely to be mixed with the enzyme layer 8. As a result, the surface of the electrode system can be covered with only the hydrophilic polymer, without any risk of possible contact with those enzymes, surfactant and electron mediator. This eliminates adverse changes in the performance of the electrode system due to adsorption of protein onto the surface of the electrode system, or chemical reaction between the electrodes and an oxidizing substance such as electron mediator, and a sensor that can respond with high accuracy is obtained.

In the cholesterol sensor of the second example, the reaction layer 8, which is composed of a layer containing enzymes and a surfactant in the cholesterol sensor of the first example, is composed of a layer 8a containing cholesterol oxidase, cholesterol esterase and further an electron mediator, which is added if occasion demands, and a layer 9a containing a surfactant for covering the layer 8a.

The layer 8a and the layer 9a can not be mixed with each other in the absence of agitation in the process of forming the layer 9a by dropping a surfactant containing solution on the layer 8a, followed by drying.

For perfect elimination of the possible chance of mutual mixing of those two layers, the solvent for dissolving the surfactant should be one, such as 2-propanol, which would not dissolve the enzyme layer. Separation of the enzyme layer from the surfactant layer suppresses the effect of the surfactant on the electrode system. This structure permits introduction of more surfactant into the surfactant layer.

In this structure, however, since homogeneous mixing of the enzyme, cholesterol esterase, with the surfactant is difficult upon an approach of the sample solution to the reaction layer, the response of the cholesterol sensor is slightly inferior compared to the cholesterol sensor of the first example. However, the use of a surfactant, such as sodium cholate, which facilitates smooth introduction of the sample solution is convenient, because it omits the process of coating the enzyme layer with the lipid layer.

Figure 4:
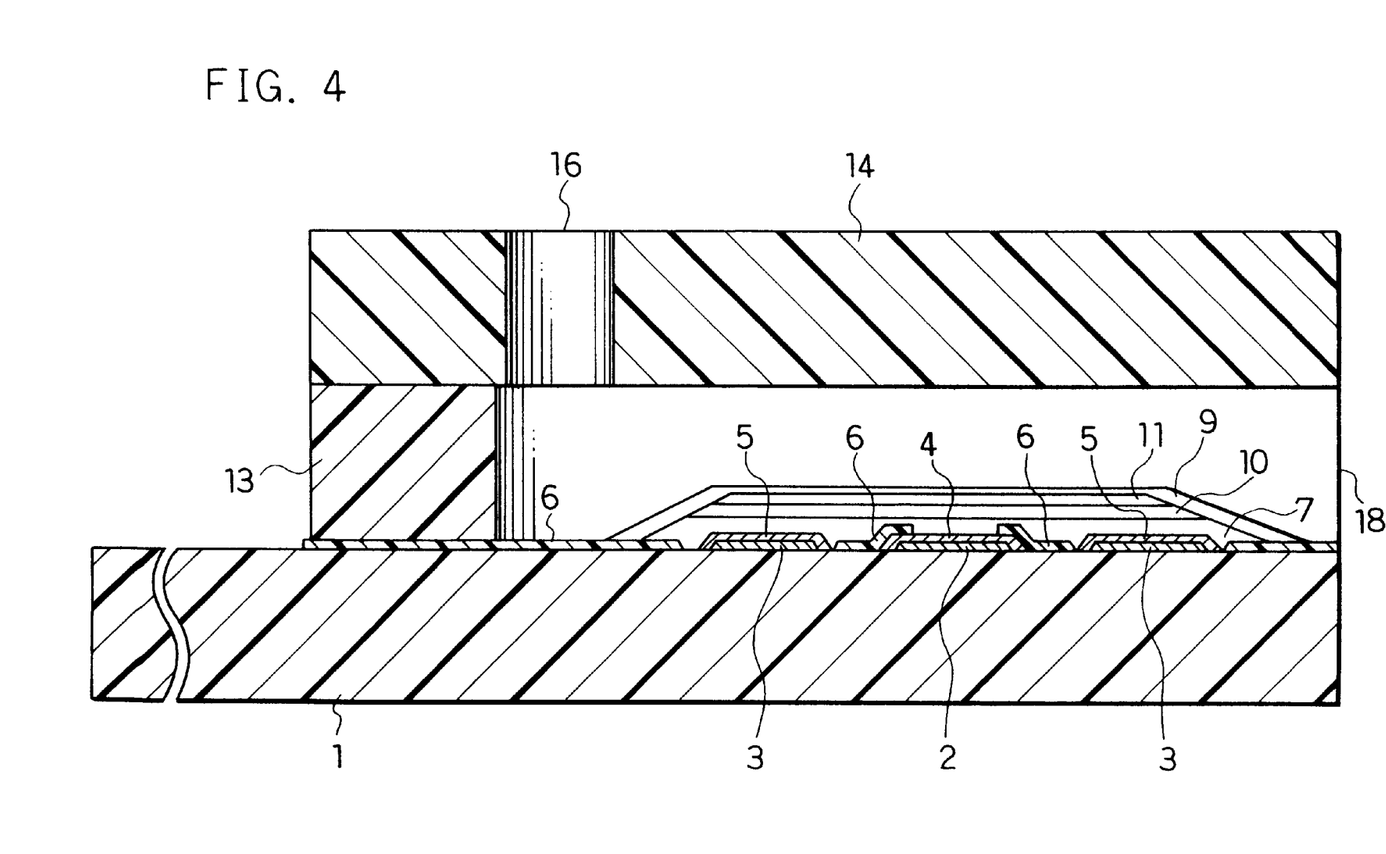
FIG. 4 is a longitudinal cross-sectional view illustrating the vital parts of a cholesterol sensor of another example in accordance with the present invention.

FIG. 4 shows a structure of a cholesterol sensor of a third example in accordance with the present invention.

As in FIG. 3, the electrically insulating base plate 1 is disposed with the leads 2 and 3, the measuring electrode 4, the counter electrode 5, the electrically insulating layer 6, and the hydrophilic polymer layer 7. Another layer 10 containing cholesterol oxidase is formed by dropping a solution containing cholesterol oxidase on the hydrophilic polymer layer 7, followed by drying. A layer 11 that contains cholesterol esterase and a surfactant is further formed on the layer 10 by dropping a solution containing these substances on the layer 10, followed by drying. Those two layers 10 and 11 are covered with the lipid layer 9 as in FIG. 3.

In the structure in which the enzyme layer is composed of two different layers, that is, the cholesterol oxidase layer 10 and the cholesterol esterase plus surfactant layer 11, the surfactant can be distributed more densely in the vicinity of cholesterol esterase and the catalytic activity of cholesterol esterase is increased. This produces an effect of rapid conversion of cholesterol ester into cholesterol when a sample solution reaches and contacts the reaction layer.

Figure 5:
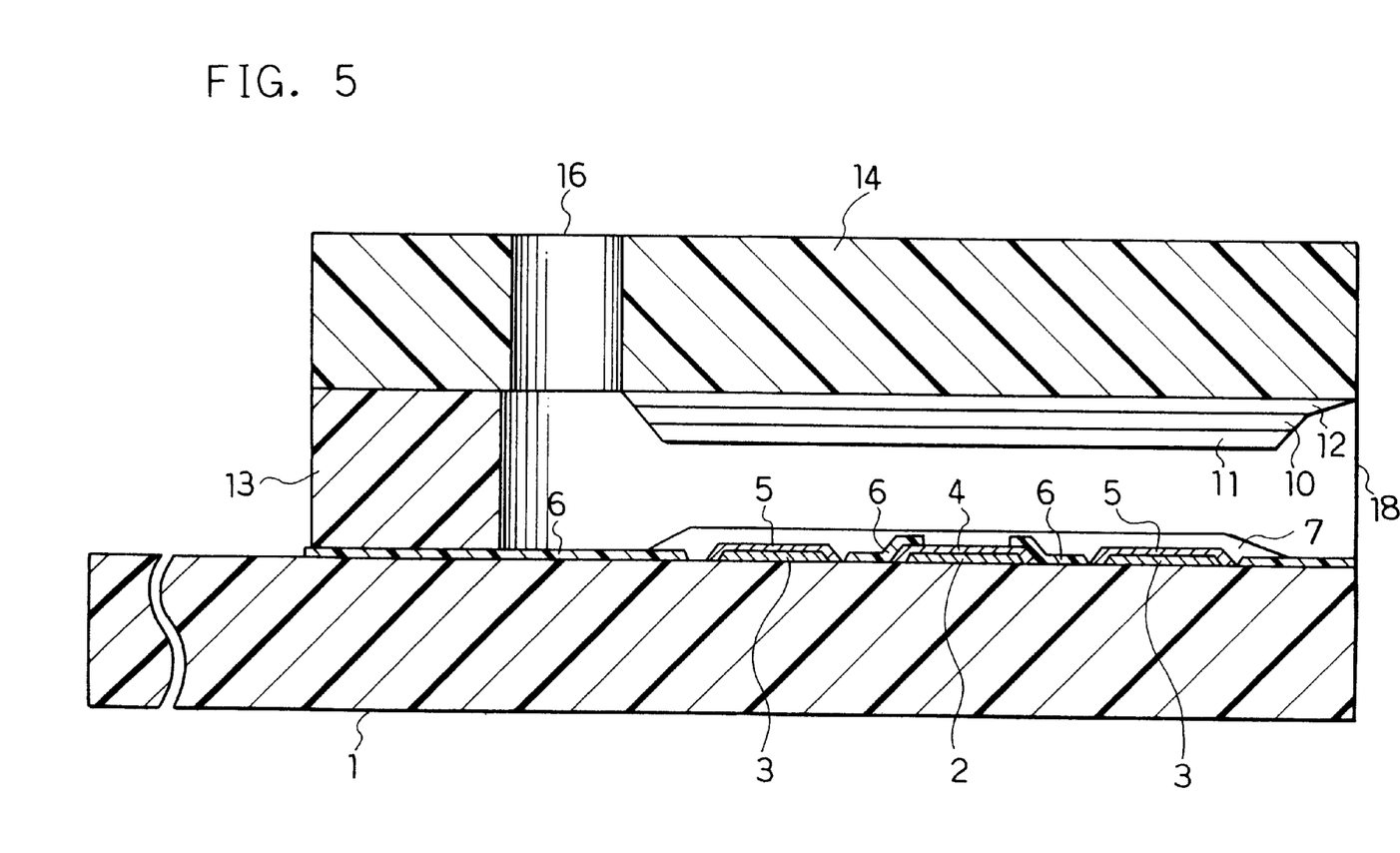
FIG. 5 is a longitudinal cross-sectional view illustrating the vital parts of a cholesterol sensor of still another example in accordance with the present invention.

FIG. 5 shows a structure of a cholesterol sensor of a fourth example in accordance with the present invention.

As in FIG. 3, the electrically insulating base plate 1 is disposed with the leads 2 and 3, the measuring electrode 4, the counter electrode 5, the electrically insulating layer 6, and the hydrophilic polymer layer 7 in close contact with the electrode system. Another hydrophilic polymer layer 12 is formed on a surface 17 of the cover exposed to a space for constituting a sample solution supply pathway. The cholesterol oxidase layer 10 and the cholesterol esterase plus surfactant layer 11 are formed on the hydrophilic polymer layer 12.

By disposing the reaction layer on the surface 17 of the cover, it becomes possible to cover the surface of the electrode system with a filter, such as a porous polycarbonate film, a polymer gel or the like. The filter is effective for preventing the hemocytes from interfering with the electrode system. This structure also permits positioning of the surfactant layer spaced from the electrode system, so that the adverse effect of the surfactant on the electrode system can be suppressed.

Positioning of the hydrophilic polymer layer on the surface of the cover suppresses separation of the reaction layer. The hydrophilic polymer layer formed on the electrode system suppresses adsorption of enzymes onto the electrodes, which is effective for preventing the influence of vibration on the measurement.

Figure 6:
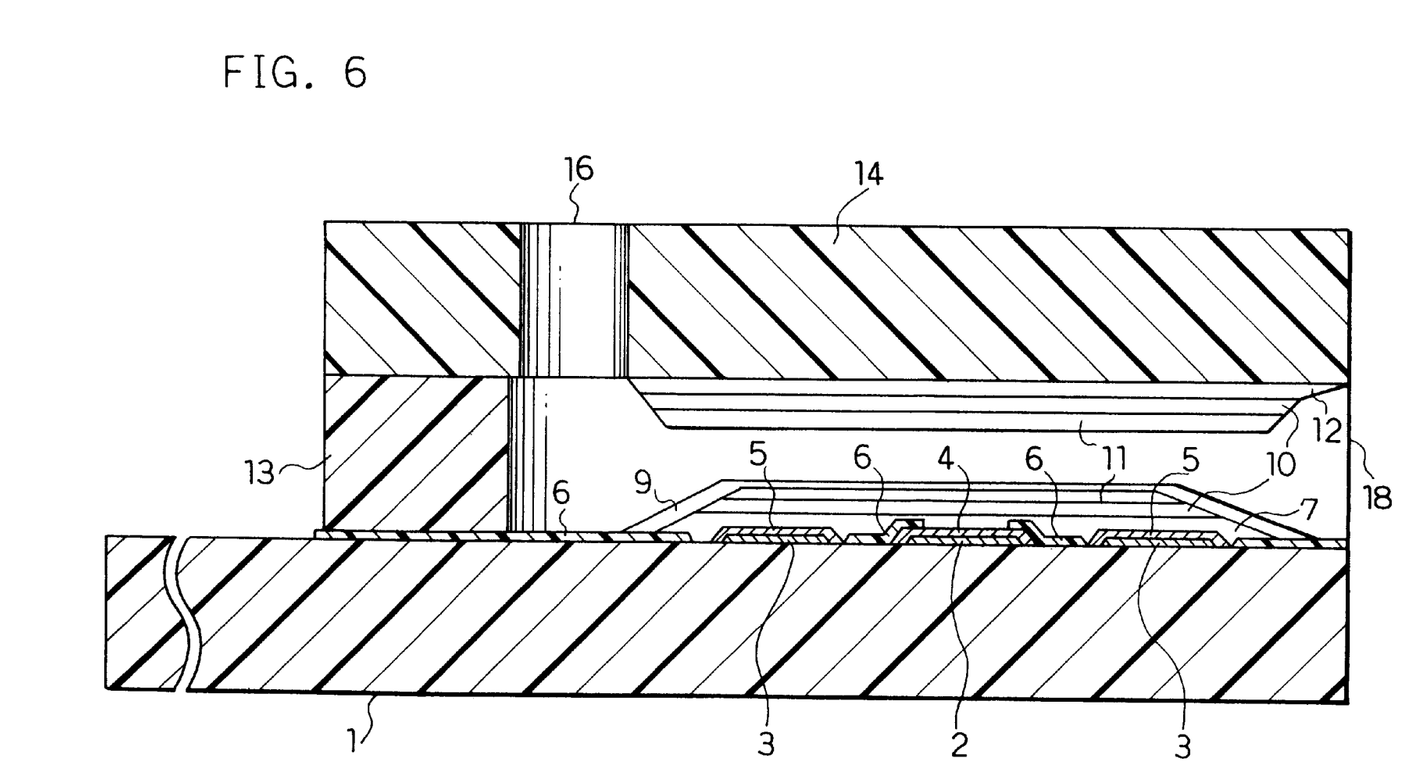
FIG. 6 is a longitudinal cross-sectional view illustrating the vital parts of a cholesterol sensor of still another example in accordance with the present invention.

FIG. 6 shows a structure of a cholesterol sensor of a fifth example in accordance with the present invention.

As in FIG. 3, the electrically insulating base plate 1 is disposed with the leads 2 and 3, the measuring electrode 4, the counter electrode 5, the electrically insulating layer 6, and the hydrophilic polymer layer 7 in close contact with the electrode system. Another hydrophilic polymer layer 12 is formed on the surface 17 of the cover exposed to a space for constituting a sample solution supply pathway. The cholesterol oxidase layer 10 and the cholesterol esterase plus surfactant layer 11 are formed in the same manner as in FIG. 4, on the hydrophilic polymer layers 7 and 12, respectively. The reaction layer formed on the electrode system is covered with the lipid layer 9 as in FIG. 3.

Positioning of the two reaction layers at different sites, one proximal to the electrode system and the other spaced from the electrode system, increases the amount of supported agents, which may result in more accelerated enzyme reaction.

In the following, the present invention will be described more specifically by way of examples.

EXAMPLE 1

In the present example, a cholesterol sensor as illustrated in FIG. 3 was produced in the below-mentioned manner.

First, 5 µl of an aqueous solution of sodium salt of a hydrophilic polymer carboxymethyl cellulose (hereinafter abbreviated to "CMC"; concentration, 0.5 wt %) was dropped over an electrode system disposed on the base plate 1, which was then dried in a hot dryer at 50° C. for 10 min to form the CMC layer 7. Subsequently, a Nocardia-derived enzyme cholesterol oxidase (hereinafter abbreviated to "ChOD") and Pseudomonas-derived cholesterol esterase (hereinafter abbreviated to "ChE"), an electron mediator potassium ferricyanide, and a surfactant n-octyl-β-D-thioglucoside were dissolved in water. The resultant aqueous solution was dropped over the previously formed CMC layer 7 and dried at 50° C. for 15 min to form the enzyme layer 8. Then, 5 µl of a toluene solution containing phosphatidyl choline (concentration, 0.5 wt %) was dropped over the enzyme layer 8 and dried to form the lipid layer 9 for covering the surface of the enzyme layer 8.

Finally, the cover 14 and the spacer 13 were adhered to the base plate 1 in a positional relationship as shown by the dotted line in FIG. 1, which gave a cholesterol sensor of this example.

To this cholesterol sensor, a cholesterol standard solution (3 µl) containing cholesterol and one kind of cholesterol ester, cholesterol linoleate, was supplied from an opening 18 of the sample solution supply pathway. Nine min later, a pulse voltage of +0.5 V was applied to the sensor toward the anode of the measuring electrode with reference to the counter electrode and the current value across the measuring electrode and the counter electrode was measured after 5 sec. In this way, the response of the cholesterol sensor to the cholesterol standard solution was evaluated.

EXAMPLE 2

In the present example, a cholesterol sensor as illustrated in FIG. 3 was produced in the below-mentioned manner.

First, the CMC layer 7 was formed on the electrode system in the same manner as in Example 1. Then, a mixture solution containing Nocardia-derived ChOD, calf pancreas-derived ChE, and potassium ferricyanide was dropped over the previously formed CMC layer 7 and dried in a hot dryer at 50° C. for 15 min to form the enzyme layer 8a, which was then dropped thereon with a 2-propanol solution containing sodium cholate (concentration, 0.5 wt %) and dried to form the surfactant layer 9a for covering the layer 8a.

Figure 7:
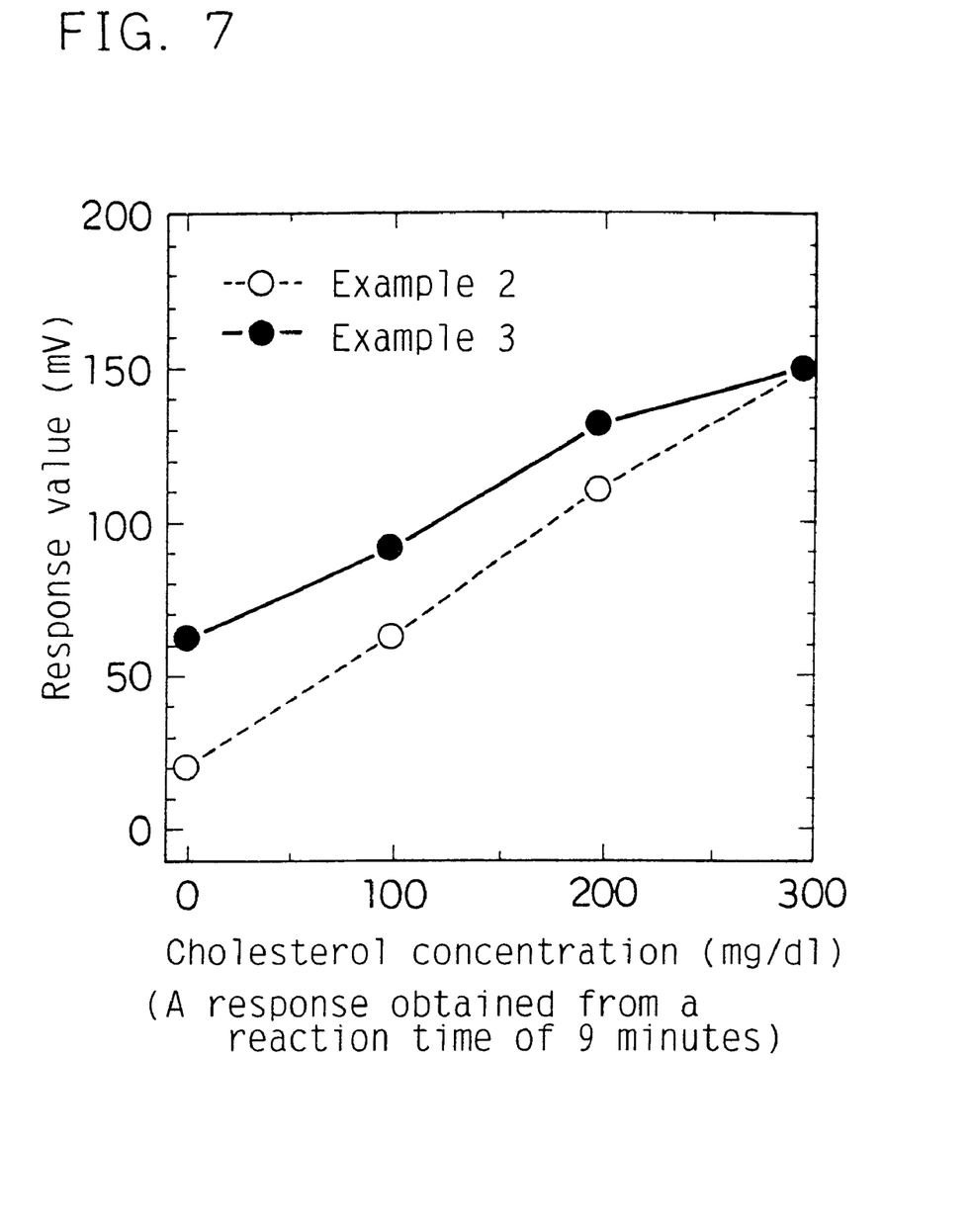
FIG. 7 is a diagram showing representative responses to standard cholesterol sample solution observed in a cholesterol sensor of one example in accordance with the present invention.

In this way, a cholesterol sensor of Example 2 was produced and the sensor response to the cholesterol standard solution was evaluated in the same manner as in Example 1. The results are shown in FIG. 7.

EXAMPLE 3

In the present example, a cholesterol sensor as illustrated in FIG. 3 was produced in the below-mentioned manner.

First, the CMC layer 7 was formed on the electrode system in the same manner as in Example 1. Then, a mixture solution containing Nocardia-derived ChOD, Pseudomonas-derived ChE, and potassium ferricyanide was dropped over the previously formed CMC layer 7 and dried in a hot dryer at 50° C. for 15 min to form the enzyme layer 8a, which was then dropped thereon with an aqueous solution of n-octyl-β-D-thioglucoside and dried to form the surfactant layer 9a for covering the layer 8a.

In this way, a cholesterol sensor of Example 3 was produced and the sensor response to the cholesterol standard solution was evaluated in the same manner as in Example 1. The results are also shown in FIG. 7.

EXAMPLE 4

In the present example, a cholesterol sensor as illustrated in FIG. 4 was produced in the below-mentioned manner.

First, the CMC layer 7 was formed on the electrode system disposed on the base plate 1 in the same manner as in Example 1. Then, a mixture solution containing Nocardia-derived ChOD and potassium ferricyanide was dropped over the previously formed CMC layer 7 and dried to form the ChOD plus potassium ferricyanide layer 10. Subsequently, a mixture solution containing Pseudomonas-derived ChE and n-octyl-β-D-thioglucoside was dropped on the layer 10 and dried at 50° C. for 15 min to form the layer 11 of ChE and n-octyl-β-D-thioglucoside. A toluene solution containing lecithin (concentration, 0.5 wt %) was further dropped over the layer 11 and dried to form the lipid layer 9.

In this way, a cholesterol sensor of Example 4 was produced and the sensor response to the cholesterol standard solution was evaluated in the same manner as in Example 1.

EXAMPLE 5

In the present example, a cholesterol sensor as illustrated in FIG. 5 was produced in the below-mentioned manner.

First, the CMC layer 7 was formed on the electrode system disposed on the base plate 1 in the same manner as in Example 1. At that time, 5 µl of an aqueous solution containing CMC (concentration, 0.5 wt %) was also dropped over the surface 17 of the cover exposed to the space for constituting the sample solution supply pathway and dried to form another CMC layer 12. Then, a mixture solution containing Nocardia-derived ChOD and potassium ferricyanide was dropped over the CMC layer 12 and dried to form the ChOD plus potassium ferricyanide layer 10. Subsequently, a mixture solution containing Pseudomonas-derived ChE and n-octyl-β-D-thioglucoside was dropped on the layer 10 and dried at 50° C. for 15 min to form the layer 11 of ChE and n-octyl-β-D-thioglucoside.

In this way, a cholesterol sensor of Example 5 was produced and the sensor response to the cholesterol standard solution was evaluated in the same manner as in Example 1.

EXAMPLE 6

In the present example, in place of the layers 10 and 11 formed in Example 5, an enzyme layer was formed on the CMC layer 12 by dropping thereon a mixture solution containing Nocardia-derived ChOD, potassium ferricyanide, Pseudomonas-derived ChE and n-octyl-β-D-thioglucoside, followed by drying.

In this way, a cholesterol sensor of Example 6 was produced and the sensor response to the cholesterol standard solution was evaluated in the same manner as in Example 1.

EXAMPLE 7

In the present example, a cholesterol sensor as shown in FIG. 6 was produced.

First, the CMC layer 7, the layer 10 and the layer 11 were formed on the electrode system disposed on the base plate 1 in the same manner as in Example 4. Then, another CMC layer 12, the layer 10 and the layer 11 were also formed over the surface 17 of the cover exposed to the space for constituting the sample solution supply pathway in the same manner as in Example 5.

In this way, a cholesterol sensor of Example 7 was produced and the sensor response to the cholesterol standard solution was evaluated in the same manner as in Example 1.

In all the cholesterol sensors in accordance with the present invention, the sensor response to the cholesterol standard solution depicted a satisfactory linear relationship with the sum of the molar concentrations of cholesterol and cholesterol ester, that is, the total cholesterol concentration.

As apparent from FIG. 7, the cholesterol sensor of Example 2 that uses 2-propanol, which does not dissolve the enzyme layer, as the solvent for dissolving the surfactant shows a current value close to 0 mV in response to the cholesterol sample solution at a concentration of 0 mg/dl, compared to the cholesterol sensor of Example 3 that uses water, which dissolves the enzyme layer, as the solvent for the surfactant. This may be because perfect separation of the enzyme layer from the surfactant layer in the cholesterol sensor of Example 2 effectively suppressed the adverse influence of the surfactant on the electrode system.

As discussed above, according to the present invention, the enzymes that express enzyme activities by mediation of a surfactant can be reacted effectively in a cholesterol sensor. As a result, a cholesterol sensor which permits short time measurements can be obtained.

Although the present invention has been described in terms of the presently preferred embodiments, it is to be understood that such disclosure is not to be interpreted as limiting. Various alterations and modifications will no doubt become apparent to those skilled in the art to which the present invention pertains, after having read the above disclosure. Accordingly, it is intended that the appended claims be interpreted as covering all alterations and modifications as fall within the true spirit and scope of the invention.

What is claimed is:

1. A cholesterol sensor comprising:
   an electrically insulating base plate;
   an electrode system composed of at least a measuring electrode and a counter electrode and disposed on said base plate, and
   a dry reaction layer formed on said electrode system,
   wherein said reaction layer contains cholesterol oxidase, cholesterol esterase and a surfactant,
   wherein said reaction layer is water soluble,
   wherein said electrode system comprises a silver coating and a carbon coating on said silver coating, and
   wherein said reaction layer comprises at least two layers, a surfactant-free layer formed on said electrode system and a layer containing a surfactant.

2. The cholesterol sensor in accordance with claim 1, wherein said surfactant-free layer comprises a hydrophilic polymer.

3. The cholesterol sensor in accordance with claim 1, wherein said reaction layer comprises a layer containing a mixture of at least cholesterol esterase and a surfactant.

4. The cholesterol sensor in accordance with claim 1, wherein said cholesterol esterase is a Pseudomonas-derived cholesterol esterase and said surfactant is at least one selected from the group consisting of n-octyl-β-D-thioglucoside, polyethylene glycol monododecylether, sodium cholate, dodecyl-β-maltoside, sucrose monolaurate, polyoxyehtylene-p-t-octylphenylether and N,N-bis(3-D-gluconamidopropyl)cholamide.

5. The cholesterol sensor in accordance with claim 1, wherein said cholesterol esterase is a mammalian pancreas-derived cholesterol esterase and said surfactant is at least one selected from the group consisting of sodium cholate, sodium deoxycholate, sodium taurodeoxycholate, N,N-bis(3-D-gluconamidopropyl)cholamide, N,N-bis(3-D-gluconamidopropyl)deoxycholamide, polyoxyehtylene-p-t-octylphenylether, polyethylene glycol monododecylether and sucrose monolaurate.

6. The cholesterol sensor in accordance with claim 1, wherein said reaction layer contains an electron mediator.

7. The cholesterol sensor in accordance with claim 1, wherein a cover member is provided to form a sample solution supply pathway for supplying a sample solution to said electrode system between said base plate and said cover member by integrating it with said base plate, two hydrophilic polymer layers are formed, one on a surface exposed to the sample solution supply pathway formed by said cover member and the other on said electrode system, and said reaction layer is formed on the former hydrophilic polymer layer.

8. A cholesterol sensor comprising:
   an electrically insulating base plate,
   an electrode system composed of at least a measuring electrode and a counter electrode and disposed on said base plate, and
   a dry reaction layer formed on or in the vicinity of said electrode system,
   wherein said reaction layer contains cholesterol oxidase, cholesterol esterase and a surfactant,
   wherein said reaction layer is water soluble,
   wherein said electrode system comprises a silver coating and a carbon coating on said silver coating,
   wherein a cover member is provided to form a sample solution supply pathway for supplying a sample solution to said electrode system between said base plate and said cover member by integrating it with said base plate, two hydrophilic polymer layers are formed, a first hydrophilic polymer layer is formed on a surface exposed to the sample solution supply pathway formed by said cover member and a second hydrophilic polymer layer is formed on said electrode system, and said reaction layer is split into a first segment and a second segment and formed, respectively, on said two hydrophilic polymer layers, wherein said first segment formed on said first hydrophilic polymer layer contains a surfactant and said second segment formed on said second hydrophilic polymer layer does not contain a surfactant.

9. A cholesterol sensor comprising:

an electrically insulating base plate, an electrode system composed of at least a measuring electrode and a counter electrode and disposed on said base plate, and a dry reaction layer formed on or in the vicinity of said electrode system, wherein said reaction layer contains cholesterol oxidase, cholesterol esterase and a surfactant, wherein said electrode system comprises silver and carbon for coating said silver, wherein said reaction layer comprises two layers, a layer containing cholesterol oxidase and cholesterol esterase only omitting a surfactant and a layer containing a surfactant and covering the former layer.

10. The cholesterol sensor in accordance with claim 9, wherein said layer containing a surfactant has been formed by adding aliquots of a solution prepared by dissolving a surfactant in a solvent that would not dissolve said layer containing cholesterol oxidase and cholesterol esterase, followed by drying.

11. The cholesterol sensor in accordance with claim 9, further comprising a layer containing hydrophilic polymer formed on said electrode system.

12. The cholesterol sensor in accordance with claim 9, wherein a cover member is provided to form a sample solution supply pathway for supplying a sample solution to said electrode system between said base plate and said cover member by integrating it with said base plate, two hydrophilic polymers are formed, one on a surface exposed to the sample solution supply pathway formed by said cover member and the other on said electrode system, and said reaction layer is formed on the former hydrophilic polymer layer.

13. The cholesterol sensor in accordance with claim 9,
wherein a cover member is provided to form a sample solution supply pathway for supplying a sample solution to said electrode system between said base plate and said cover member by integrating it with said base plate, two hydrophilic polymer layers are formed, a first hydrophilic polymer layer formed on a surface exposed to the sample solution supply pathway formed by said cover member and a second hydrophilic polymer layer formed on said electrode system, and said reaction layer is split into a first segment and a second segment and formed, respectively, on said two hydrophilic polymer layers.

14. The cholesterol sensor in accordance with claim 9, wherein said cholesterol esterase is a Pseudomonas-derived cholesterol esterase and said surfactant is at least one selected from the group consisting of n-octyl-β-D-thioglucoside, polyethylene glycol monododecylether, sodium cholate, dodecyl-β-maltoside, sucrose monolaurate, polyoxyethylene-p-t-octylphenylether and N,N-bis(3-D-gluconamidopropyl)cholamide.

15. The cholesterol sensor in accordance with claim 9, wherein said cholesterol esterase is a mammalian pancreas-derived cholesterol esterase and said surfactant is at least one selected from the group consisting of sodium cholate, sodium deoxycholate, sodium taurodeoxycholate, N,N-bis(3-D-gluconamidopropyl)cholamide, N,N-bis(3-D-gluconamidopropyl)deoxycholamide, polyoxyethylene-p-t-octylphenylether, polyethylene glycol monododecylether and sucrose monolaurate.

16. The cholesterol sensor in accordance with claim 9, wherein said reaction layer contains an electron mediator.

17. A cholesterol sensor comprising:

an electrically insulating base plate, an electrode system composed of at least a measuring electrode and a counter electrode and disposed on said base plate, and a dry reaction layer formed on or in the vicinity of said electrode system, wherein said reaction layer contains cholesterol oxidase, cholesterol esterase and a surfactant, wherein said reaction layer comprises a layer of cholesterol oxidase and cholesterol esterase omitting a surfactant and a layer containing a surfactant and covering the former layer, wherein said electrode system comprises a silver coating and a carbon coating on said silver coating, and wherein said reaction layer is water soluble.

18. The cholesterol sensor in accordance with claim 17, further comprising a layer containing hydrophilic polymer formed on said electrode system.

19. The cholesterol sensor in accordance with claim 17, wherein a cover member is provided to form a sample solution supply pathway for supplying a sample solution to said electrode system between said base plate and said cover member by integrating it with said base plate, two hydrophilic polymers are formed, one on a surface exposed to the sample solution supply pathway formed by said cover member and the other on said electrode system, and said reaction layer is formed on the former hydrophilic polymer layer.

20. The cholesterol sensor in accordance with claim 17,
wherein a cover member is provided to form a sample solution supply pathway for supplying a sample solution to said electrode system between said base plate and said cover member by integrating it with said base plate, two hydrophilic polymer layers are formed, a first hydrophilic polymer layer formed on a surface exposed to the sample solution supply pathway formed by said cover member and a second hydrophilic polymer layer formed on said electrode system, and said reaction layer is split into a first segment and a second segment and formed, respectively, on said two hydrophilic polymer layers.

21. The cholesterol sensor in accordance with claim 17, wherein said cholesterol esterase is a Pseudomonas-derived cholesterol esterase and said surfactant is at least one selected from the group consisting of n-octyl-β-D-thioglucoside, polyethylene glycol monododecylether, sodium cholate, dodecyl-β-maltoside, sucrose monolaurate, polyoxyethylene-p-t-octylphenylether and N,N-bis(3-D-gluconamidopropyl)cholamide.

22. The cholesterol sensor in accordance with claim 17, wherein said cholesterol esterase is a mammalian pancreas-derived cholesterol esterase and said surfactant is at least one selected from the group consisting of sodium cholate, sodium deoxycholate, sodium taurodeoxycholate, N,N-bis(3-D-gluconamidopropyl)cholarnide, N,N-bis(3-D-gluconamidopropyl)deoxycholamide, polyoxyethylene-p-t-octylphenylether, polyethlene glycol monododecylether and sucrose monolaurate.

23. The cholesterol sensor in accordance with claim 17, wherein said reaction layer contains an electron mediator.

24. A method for producing a cholesterol sensor comprising the steps of:

forming an electrode system by printing a silver paste on an electrically insulating base plate and further printing a carbon paste thereon to cover said silver paste, forming a hydrophilic polymer layer on said electrode system by dropping thereon a solution containing a hydrophilic polymer, forming an enzyme layer by adding aliquots of a solution containing at least cholesterol oxidase and cholesterol esterase but no surfactant over said hydrophilic polymer layer, followed by drying, and forming a surfactant layer on said enzyme layer, wherein said surfactant layer is formed by adding aliquots of a solution prepared by dissolving a surfactant in a solvent that would not dissolve said enzyme layer, followed by drying.

25. A cholesterol sensor comprising:

an electrically insulating base plate, an electrode system composed of at least a measuring electrode and a counter electrode and disposed on said base plate, and a dry reaction layer formed on or in the vicinity of said electrode system, wherein said reaction layer contains cholesterol oxidase, cholesterol esterase and a surfactant, wherein said reaction layer is water soluble, wherein said electrode system comprises a silver coating and a carbon coating on said silver coating, wherein a cover member is provided to form a sample solution supply pathway for supplying a sample solution to said electrode system between said base plate and said cover member by integrating it with said base plate, and wherein said reaction layer comprises at least two layers, a surfactant-free layer formed on said electrode system and a layer containing a surfactant.

* * * * *